United States Patent [19]

DeMello et al.

[11] Patent Number: 4,863,442
[45] Date of Patent: Sep. 5, 1989

[54] SOFT TIP CATHETER

[75] Inventors: Richard M. DeMello, Acton; Robert J. Ham, Saugus; Michael Lang, Westford; Gerry D. Ouellette, Framingham; Andrea T. Slater, Tyngsboro; Frederick W. Trombley, III, Billerica, all of Mass.

[73] Assignee: C. R. Bard, Inc., Murray Hill, N.J.

[21] Appl. No.: 85,392

[22] Filed: Aug. 14, 1987

[51] Int. Cl.$^4$ .............................................. A61M 25/00
[52] U.S. Cl. ......................................................... 604/282
[58] Field of Search .................. 604/96, 275, 280, 281, 604/282, 283, 284, 103, 95; 128/656, 657, 658

[56] References Cited

U.S. PATENT DOCUMENTS

| | | | |
|---|---|---|---|
| 1,699,590 | 1/1929 | Ireland | 604/275 |
| 3,485,234 | 12/1969 | Stevens | 604/281 |
| 3,618,614 | 11/1971 | Flynn | 604/282 |
| 3,890,976 | 6/1975 | Bazell et al. | 604/96 |
| 3,924,637 | 12/1975 | Cook | 604/282 |
| 4,044,765 | 8/1977 | Kline | 604/282 |
| 4,052,989 | 10/1977 | Kline | 604/282 |
| 4,425,919 | 1/1984 | Alston, Jr. et al. | 604/282 |
| 4,430,083 | 2/1984 | Ganz et al. | 604/283 |
| 4,447,239 | 5/1984 | Krotten | 604/282 |
| 4,516,972 | 5/1985 | Samson | 604/282 |
| 4,547,193 | 10/1985 | Rydell | 604/282 |
| 4,563,181 | 1/1986 | Wijayamthna et al. | 128/656 |
| 4,596,563 | 6/1986 | Pande | 604/280 |
| 4,636,346 | 1/1987 | Gold et al. | 604/280 |
| 4,690,175 | 9/1987 | Ouchi et al. | 604/282 |

FOREIGN PATENT DOCUMENTS

WO87/07493 12/1987 PCT Int'l Appl. ................ 128/656

Primary Examiner—John D. Yasko
Attorney, Agent, or Firm—Wolf Greenfield & Sacks

[57] ABSTRACT

A guide catheter having a tubular body with a wire-braided Teflon core and a polyurethane jacket. The distal end of the jacket is removed from the core, and a soft polyurethane tip is applied to the core over the region where the jacket has been removed. The tip overlaps the core for approximately two millimeters and extends distally approximately two millimeters beyond the distal end of the core. The tip may be applied to the core as a separate tube bonded to it or be built up on the core by repeatedly dipping the top in a polyurethane slurry, or be molded onto the distal end of the core.

22 Claims, 2 Drawing Sheets

SOFT TIP CATHETER

INTRODUCTION

This invention relates to catheters and more particularly relates to guide catheters and their method of manufacture.

Typical functions of a guide catheter are to provide an access pathway for the delivery of a dilatation catheter to the coronary vasculature and to act as a support for the dilatation catheter during coronary angioplasty. To perform those functions, the catheter must be capable of safely reaching the coronary ostium. Catheterization of the coronary arteries is a very delicate procedure which sometimes causes vascular trauma and/or creates embolisms with devastating consequences for the patient.

The principal object of the present invention is to provide a guide catheter with a soft tip so as to reduce the frequency of vascular complications.

PRIOR ART

In U.S. Pat. No. 4,551,292 and 4,531,943 assigned to Angiomedics Corporation, a soft tip angiographic catheter and a method of manufacturing it are described. The angiographic catheter which is the subject matter of those patents has a soft distal tip with a circumferential preferential fold line, which causes the tip to collapse in a predetermined fashion whenever the tip engages an obstruction. The circumferential preferential fold line is formed by a cylindrical wire having a protuberance of a predetermined shape, which is inserted into the distal end of the catheter body so as to expand the catheter material. The catheter material is heated with the cylindrical wire in place to form the preferential fold line. This procedure provides the catheter with a bulbous tip at its distal end having a diameter which exceeds the diameter of the main tubular portion of the catheter. This construction has at least two disadvantages, namely, the enlarged tip makes it more difficult to insert the catheter into the blood vessel through the percutaneous introducer and it impedes blood flow around the catheter to the coronary arteries.

U.S. Pat. No. 4,636,346 dated Jan. 13, 1987 and assigned to Cordis Corporation discloses a soft tipped guide catheter that includes a tubular body having an interior lubricious sheath, an intermediate, relatively stiff sheath and a flexible outer sheath, and a tip having an interior lubricious sheath and a flexible outer sheath made of the same material as the outer sheath of the tubular body. In one embodiment, the tip may initially be formed as a separate member and then affixed end to end to the tubular body by such techniques as heat, adhesive, etc. with the assistance of a shrink film. In another embodiment, the distal end of the body is ground down to remove the intermediate and outer sheaths of the body, and the tip is slipped over the ground portion affixed to it with the aid of heat, shrink film, adhesive, etc. In this form, the tip and tubular body share the same inner sheath. In a third embodiment, the tip is integrally extended with the inner and outer sheaths of the tubular body while the intermediate sheath is interrupted at the tip region. The tip softness in all these embodiments is essentially the same as the outer sheath of the body, and therefore the protection provided is limited. Furthermore, the tip material is not provided at its distal end with a substantial overlapping of the relatively stiff core of the tubular body, and consequently the bonding of the tip to the body is not always effective.

In Cordis U.S. Pat. No. 4,596,563, a catheter with a flexible tip is described having a tubular body made up of a rigid inner sheath and a relatively flexible outer sheath. The flexible tip is formed by extending the outer sheath distally beyond the inner sheath. Like the '346 Cordis patent, supra, the tip has the same hardness as the sheath or outer jacket of the tubular body.

U.S. Pat. No. 4,385,635 issued to Ruiz discloses an angiographic catheter having a main tubular body, an intermediate zone and a tip zone. The main tubular body is reinforced with an inner ply of polyamide material which diminishes in thickness through the intermediate zone to zero at the tip. As with the Cordis '563 patent, supra, the tip has the same softness as the jacket of the main tubular body portion.

In the U.S. Pat. No. 4,563,181 assigned to Mallinckrodt, Inc., another soft tip intravascular catheter is shown wherein the tip made of a nylon blend is fused or welded at a butt joint to the tubular body made of a different, stiffer nylon. That type of connection, as mentioned above, is sometimes ineffective.

Other U.S. patents showing catheters with soft tips are U.S. Pat. Nos. 4,464,176, 4,321,226, 4,282,876 and 3,890,976.

SUMMARY OF INVENTION

In accordance with the present invention, the soft tip catheter has no preferential fold line, and its outer diameter at the tip does not exceed the outer diameter of the main body of the guide catheter. Rather, the catheter of the present invention has essentially a uniform outer diameter throughout its axial extent. Consequently, the tip of the catheter of the present invention will pass through the introducer with the same facility as the main body of the catheter, and the catheter tip will not obstruct the blood flow around the catheter to the coronary arteries. Furthermore, the inner diameter of the tip is not less than the inner diameter of the tubular body so as not to interfere with insertion of the dilatation catheter through it.

In accordance with the preferred embodiment of the present invention, the main body of the guide catheter has a reduced outer diameter at its distal end, and a soft polyurethane tip is mounted on the end portion of reduced diameter. The soft tip overlaps the distal end for approximately two millimeters and extends distally approximately two millimeters beyond the main body. In the preferred embodiment, the tip is separately fabricated as a soft polyurethane tube and attached to the main body, and the tip is then shaped in place as part of the assembly. In accordance with a second embodiment of the present invention, the tip may be developed by repeated dipping of the distal end of the main body into a semi viscous slurry of the soft polyurethane. In accordance with yet another embodiment of the present invention, the reduced diameter distal end of the main body is placed in a female mold whose cavity has been machined to the desired tip configuration. Soft polyurethane is injected into the cavity so as to mold the tip onto the body of the catheter.

The preferred embodiment of the present invention is made up of a main body composed of a polyurethane outer jacket laminated onto a wire-braided teflon core. Approximately two millimeters of the outer jacket at the distal end are stripped from the core, which forms a shoulder proximally of the end of the core, and a marker band is placed about the core against the shoulder. A soft polyurethane tube is forced over the core and may abut against the shoulder at the distal end of the jacket and overlie the marker band. A stepped mandrel is then inserted into the distal end of the assembled soft polyurethane tube and relatively stiff core with the step in the mandrel abutting the distal end of the soft polyurethane tube. A tubular shrink film is next placed over the soft polyurethane tube and the distal end of the jacket and overlies the region where the two are to be bonded. The assembly is then heated for a time and temperature sufficient to cause the soft polyurethane tube to fill the gaps about the marker band and any other gaps which may exist at the bonding area and about the mandrel so that the inner diameter of the tube conforms to the mandrel surface. The mandrel and the shrink tube are thereafter removed, the outer diameter of the assembled guide catheter may be ground smooth and the assembly may be provided with an antithrombogenic coating. Finally, the tip may be ground again so as to remove any coating which covers approximately the last two millimeters of the tip so as to preserve its soft character. The substantial overlap of the tip material on the core assures the formation of a sound bond between the body and tip.

These and other objects and features of the present invention will be better understood and appreciated from the following detailed description of several embodiments thereof, selected for purposes of illustration and shown in the accompanying drawings.

BRIEF FIGURE DESCRIPTION

FIG. 1 is a fragmentary view, partly in section showing the preferred embodiment of a guide catheter with a soft tip, constructed in accordance with this invention; and FIGS. 2A–2I are fragmentary cross-sectional views diagrammatically illustrating the sequence of steps for manufacturing the soft tip guide catheter of FIG. 1, in accordance with the present invention.

DETAILED DESCRIPTION

Figure 1:
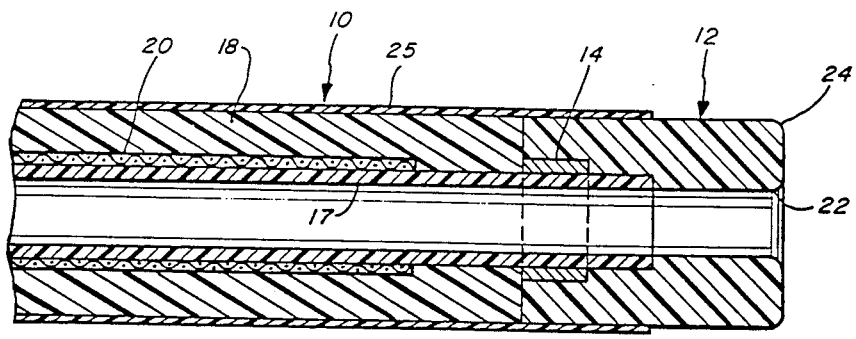

The catheter shown in FIG. 1 includes an elongated tubular body 10 and a soft tip 12 bonded to it. In the region where the body 10 and tip 12 are bonded together, a precious metal marker band 14 is provided which serves as a radiopaque identifier.

The tubular body 10 typically may be made up of a wire-braided Teflon core 16 and a polyurethane outer jacket 18 bonded together at their interface by an epoxy 20. (Teflon is a trademark of and is available from E.I. duPont de Nemours & Co., Inc.) This catheter body construction is well-known in the industry and is not per se the subject of this invention. The wire-braided Teflon core — polyurethane jacket laminate is currently used in guide catheters sold by C.R. Bard, Inc., the assignee of this application. While that particular body construction is particularly suitable for use with guide catheters because of its ability to transmit torque, its stiffness, and other characteristics, it should be understood that the catheter tubular body may be made of other materials and be uniform throughout its cross section. The Durometer of the polyurethane jacket 18 in the example given is approximately 55D while the much softer polyurethane tip 12, on the other hand, preferably has a Durometer of approximately 85A. Radii are formed in the tip at the inner and outer diameters as suggested at 22 and 24 to further reduce the likelihood of vascular trauma as the catheter passes through the blood vessels.

Preferably, the catheter assembly is provided with an antithrombogenic coating as suggested at 25. However, to preserve the softness of the tip, any coating which may have been applied to the last two millimeters of the tip at its distal end should be removed. In the tubular body described above, typically the various thicknesses of the layers may be approximately as follows: Teflon layer 17, 0.002"; epoxy 20, 0.0005"; urethane jacket 18, 0.012" and coating 25, 0.0015". Its length is approximately 40". In one size guide catheter, the inner and outer diameters of the tubular body are approximately 0.072 and 0.104 inch.

The outer diameter of the guide catheter shown in FIG. 1 is uniform throughout its length. That is, the outer diameter of the tip 12 is essentially the same as the other diameter of the tubular body 10 of the guide catheter. Consequently, it is no harder to introduce the tip 12 through an introducer (not shown) to insert the guide catheter into a patient's blood vessel than it is to project the tubular body 10 through it, and when the guide catheter is in placed in the vessel, the tip does not increase the impedance to blood flow about the catheter body.

Figure 2A:
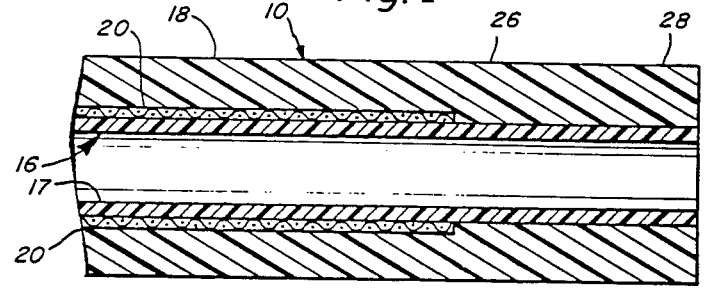

In FIGS. 2A–2I, the method of making the catheter shown in FIG. 1 is suggested. In FIG. 2A, the laminate composed of the polyurethane outer jacket 18 and the wire braided Teflon core 16 is shown. The jacket has a Durometer reading of approximately 55D. The tubular body 10 of the guide catheter normally is approximately 40 inches in length and the wire braid about the Teflon layer 17 terminates several inches from the distal end. As stated, the material is widely used in catheters for angioplasty, arteriography, etc. sold by C. R. Bard, Inc. It is ordinarily provided with a antithrombogenic coating 25 on the surface 26, and the distal end 28 is capable of being formed into a variety of curved shapes by heating and then cooling the material. The absence of the wire braid at the end facilitates the shaping of the curved end. The body 10 is capable of monitoring intravascular pressures and may be used to deliver contrast agents for vessel opacification as well as for the delivery of balloon dilatation catheters used in angioplasty.

Figure 2B:
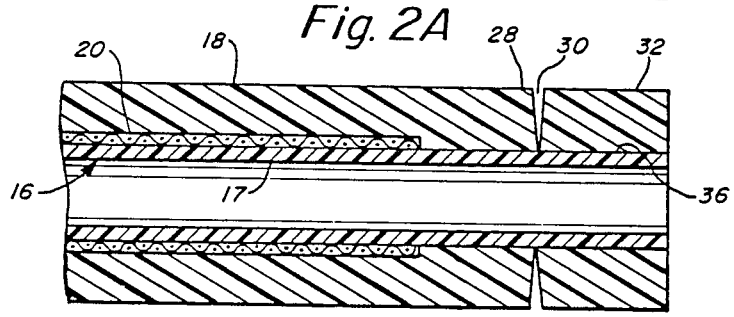
Figure 2C:
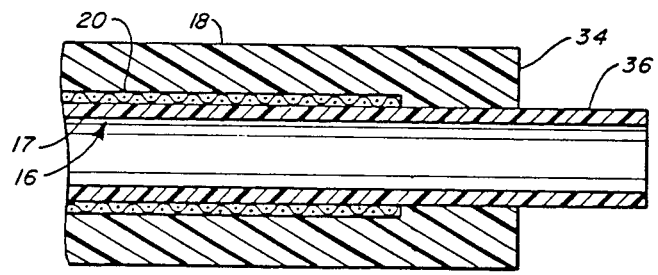

In FIG. 2B, at approximately two millimeters from the distal end 28, the catheter tubular body 10 is shown skived at 30, which enables the section 32 of the polyurethane jacket 18 and the epoxy beyond the wire braid to be stripped from the core 16. FIG. 2C illustrates the body 10 with the section 32 removed. The removal of section 32 reduces the diameter of the body 10 at the distal end and forms a shoulder 34 at the distal end of the jacket 18 extending radially from the surface 36 of the core 16.

Figure 2D:
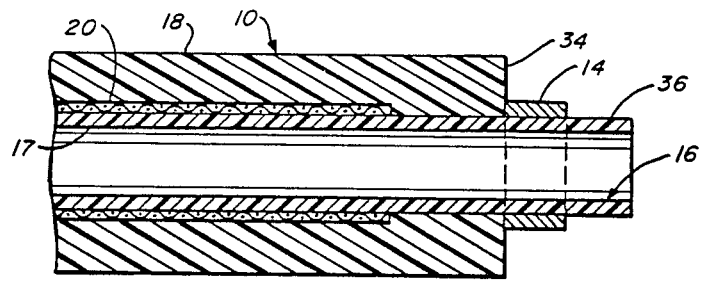

FIG. 2D shows the marker band 14 disposed on the surface 36 of the core 16 and abutting the shoulder 34. The band 14 serves as a radiopaque identifier to assist the physician in placing the distal end of the catheter at the desired location within the patient's blood vessel. Typically, the band may be made of a precious metal such as gold, platinum, etc. and have a wall thickness of approximately 0.002 and be approximately one millimeter in length.

Figure 2E:
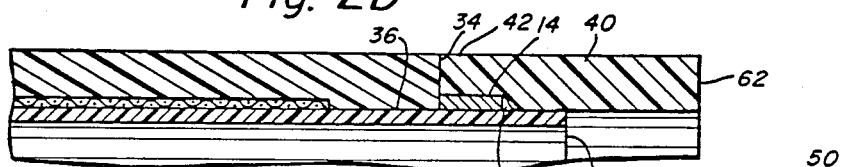

After the marker band 14 is applied, a soft polyurethane tube 40 approximately four millimeters long and from which the soft tip 12 is formed, is forced over the reduced diameter distal end of the main body 10 so that its proximal end 42 abuts against the shoulder 34. While this position is illustrated in FIG. 2E, it is to be understood that the polyurethane tube 40 may be forced onto the distal end of the main body 10 with a slight gap between the shoulder 34 and the proximal end of the tube to allow the polyurethane material of the tube 40 to flow when the assembly is heated in a later step in the manufacture of the catheter. The tube 40 extends approximately two millimeters beyond the distal end 44 of the core 16, and the proximal end 42 of the tube 40 overlaps the marker 14. In FIG. 2E, a gap 46 is suggested between inner surface of the tube 40 and the outer surface 36 of the core immediately adjacent the marker 14. As is evident from an inspection of FIG. 1, that gap is also filled during the heating step in the manufacture of the catheter.

Figure 2F:
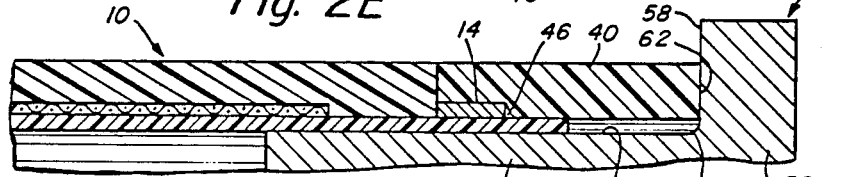

FIG. 2F illustrates the next step in the manufacturing process wherein a mandrel 50 having a section 52 with an outer diameter which essentially matches the inner the diameter of the core 16 is inserted through the tube 40 and into the core 16 so as to extend proximally at least to and preferably beyond the shoulder 34. The mandrel also has an enlarged portion 56 and a shoulder 58. A radius 60 is shown joining the surface 54 and the shoulder 58 of the mandrel section 52. The mandrel is inserted into the distal end of the main body 10 and tube 40 until the shoulder 58 engages the distal end 62 of the tube. The mandrel extends proximally beyond the bonding area between the tube 40 and the body 10.

Figure 2G:
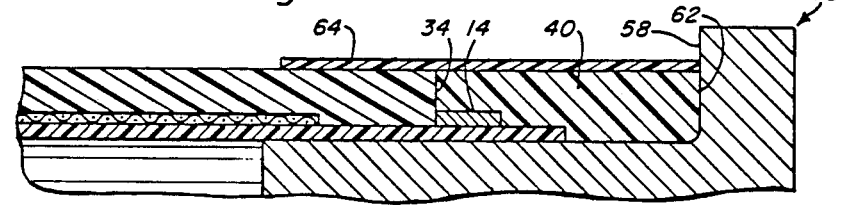
Figure 2H:
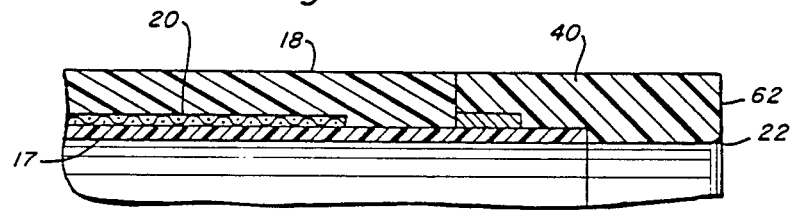

After the mandrel is inserted as shown in FIG. 2F, a sleeve of shrink film 64 is placed over the polyurethane tube 40 and the distal end of the jacket 18 and overlaps the shoulder 34. With the sleeve of shrink film 64 in place as shown in FIG. 2G, the distal end of the assembly is heated to a temperature and for a time sufficient to cause the soft polyurethane tube 40 to flow and fill the gap 46 along with any other gaps which may exist between it and the shoulder 34, outer surface 36 of the core 16, and the outer surface 54 of the mandrel 50. The time and temperature is a function of the particular polyurethane used. With one material tested, the temperature was approximately 320° for a duration of approximately five minutes. The tube 40 as a result assumes the shape shown in FIG. 2H and includes the radius 22 at the inner diameter of the tube 40 at the distal end 62. The film 64 as it shrinks under the application of heat will somewhat compress the polyurethane and cause it to conform closely to the contours of the mandrel 50. After the assembly cools, the mandrel 50 may be removed and the shrink film 64 should be stripped from the assembly. The assembled body 10, tube 40 and marker 14 are then generally configured as illustrated in FIG. 2H.

Figure 2I:
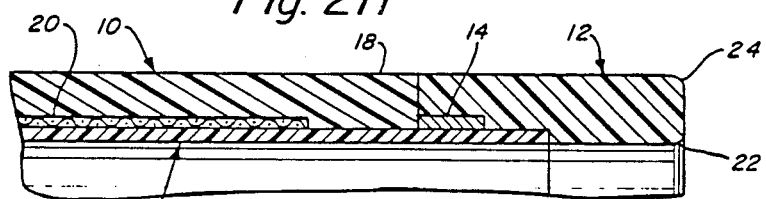

Next, the distal end of the tube 40 at the outer diameter should be ground to form the radius 24 as shown in FIG. 2I. The entire outer diameter of the assembly may then be ground to smooth the outer surface of the catheter throughout its length. Thereafter, a coating of antithrombogenic material may be applied to the outer surface. The coating should be removed from the distal end of the tip 12 for an axial distance of approximately two millimeters particularly if the coating increases the stiffness of the tip 12.

As suggested above, while the soft polyurethane tip in the preferred embodiment is applied as described by forcing a tube of the material over the stepped distal end of the main body of the catheter, the tip may be formed by other techniques. For example, the tip may be formed by applying successive coatings of soft polyurethane over the stepped distal end of the tubular body 10 with the body prepared as illustrated in FIGS. 2A-2C. This may be accomplished by forming a slurry of polyurethane composed of approximately 12% by weight of the polyurethane and 82% of a polyurethane solvent such as tetrahydrofurane (THF). With the solution at room temperature, the distal end of the body may be inserted to the depth of the shoulder 34 for a period of approximately one second and thereafter, be removed for a period of six to ten minutes to permit the slurry to partially dry. The rate at which the tip is removed from the slurry will determine the thickness of the application of the coating. The faster the tip is removed, the thicker the layer of coating which will be applied to the main body. This dipping procedure may be repeated several times (seven times in a test conducted by applicants) so as to achieve sufficient thickness for the tip. Because the material applied in this fashion shrinks significantly during the first 24 hours, it may be desirable to build up a coating or tip thickness which exceeds the diameter of the main body. The finishing of the manufacture in accordance with this method includes forming radii at the inner and outer diameters of the tip at the distal end.

In accordance with yet another method of manufacturing the soft tip guide catheter, the stepped distal end of the body prepared as shown in FIGS. 2A-2C may be inserted into a mold cavity and liquid soft polyurethane forced into the cavity. The cavity of the mold should be machined to the desired tip configuration. After the distal end of the body is placed in position in the cavity, the soft polyurethane is injected into the cavity under heat and pressure, and the material fuses to the stepped end. This manufacturing technique results in a unified shaft-soft tip product. The radii at the inner and outer diameters of the tip may be formed during the molding step so as to eliminate an additional manufacturing operation.

In the foregoing description, the invention has been described in terms of a guide catheter having a laminated main body composed of a polyurethane outer jacket and a wire-braided Teflon core. It will be appreciated that the tubular body may be uniform throughout its cross-section, and may be made of a variety of different materials. It should also be appreciated that the invention may be embodied in catheters of a variety of different sizes, and the invention will be beneficial in all those applications where vascular trauma or the creation of embolisms is of concern.

In accordance with this invention, the last few millimeters of tip (two millimeters in the embodiment described are very soft to form a bumper to protect the patient. The very soft region is confined to the tip so as not to interfere with placement of the catheter in the blood vessels or interfere with its ability to support the dilatation catheter. If the soft material extended back from the tip over the curved end, the catheter would buckle or otherwise distort when being inserted into the system and would not support a dilatation catheter.

It will also be appreciated that the scope of the invention is not confined to the specific embodiments illustrated and described herein. Rather, it is the intention of applicants that the scope of this invention be determined by the appended claims and their equivalents.

We claim:

1. An intravascular catheter comprising a main tubular body having a relatively hard Teflon core including wire braid and a generally coextensive polyurethane outer jacket, said body having proximal and distal ends, said distal end of the body having an end portion of reduced diameter distally beyond the wire braid and outer jacket but overlapping the Teflon core, and a polyurethane tubular tip made of the same material throughout and having a proximal end overlapping the reduced diameter end portion of the body and extending distally beyond the reduced diameter end of the core, said tip having an outer diameter at its proximal end substantially equal to the outer diameter of the jacket immediately adjacent said end portion and having an inner diameter distally beyond the reduced diameter end portion which is substantially equal to the inner diameter of said end portion, the material of the tip being softer than the material of the outer jacket.

2. A catheter as defined in claim 1 wherein
the diameter of the end portion is reduced by the absence of the polyurethane outer jacket from the core.

3. A catheter as defined in claim 1 wherein
the relatively soft polyurethane tip includes a plurality of layers deposited one on top of another and bonded together.

4. A catheter as defined in claim 2 wherein
the relatively soft polyurethane tip includes a plurality of layers deposited one on top of another and bonded together.

5. A catheter as defined in claim 1 wherein
the relatively soft polyurethane tip is injection molded over the end portion of the body.

6. A catheter as defined in claim 2 wherein
the relatively soft polyurethane tip is injection molded over the end portion of the body.

7. A catheter as defined in claim 1 wherein the tip overlaps the distal end of the body approximately two millimeters.

8. A catheter as defined in claim 1 wherein the tip extends distally approximately two millimeters beyond the distal end of the core.

9. An intravascular catheter comprising
a main tubular body having a relatively stiff core and a smooth outer jacket, said core extending distally beyond the end of the jacket,
and a tubular tip made of a uniform material throughout which is softer than the material of the jacket and secured to and overlapping the distal end of the core and bonded to the distal end of the jacket, said tip extending distally beyond the distal end of the core and having inner and outer diameters that are the same as the inner diameter of the core and the outer diameter of the jacket, respectively.

10. A catheter as defined in claim 9 wherein
a marker band is disposed radially within the tip and radially about the core.

11. A catheter as defined in claim 10 wherein the core is made of a wire-braided material and the jacket and tip are made of polyurethane.

12. A catheter as defined in claim 10 wherein the tip has a Durometer of approximately 85A.

13. A catheter as defined in claim 12 wherein the jacket has a Durometer of approximately 55D.

14. An intravascular catheter comprising
a main tubular body having distal and proximal ends,
a step provided at the region of the distal end of the body between a section of reduced diameter extending to the distal end of the body and the section of the body proximal thereof,
and a tubular tip made of a uniform material throughout which is softer than the material of the body, secured to and overlapping the section of reduced diameter and secured to the step in the body, said tip extending distally beyond the end of the body and having an outer diameter equal to the diameter of the body immediately proximal to the step and having an inner diameter equal to the inner diameter of the body immediately distal to the step.

15. A catheter as defined in claim 14 wherein the tip has a Durometer in the order of 85A.

16. A catheter as defined in claim 14 wherein the tip overlaps the section of reduced diameter by approximately two millimeters.

17. A catheter as defined in claim 14 wherein the tip extends distally approximately two millimeters beyond the end of the body.

18. A catheter as defined in claim 1 wherein a marker band is disposed about the proximal end of the portion of reduced diameter and under the tubular tip.

19. A catheter as defined in claim 18 wherein the tip overlaps the distal end of the body approximately two millimeters.

20. A catheter as defined in claim 18 wherein the tip extends distally approximately two millimeters beyond the distal end of the core.

21. A catheter as defined in claim 19 wherein the tip extends distally approximately two millimeters beyond the distal end of the core.

22. A catheter as defined in claim 14 wherein
a marker band is mounted on the reduced diameter portion of the body immediately distal to the step and underlies the proximal end of the tubular tip.

* * * * *